United States Patent [19]
Momose

[11] Patent Number: 5,930,325
[45] Date of Patent: Jul. 27, 1999

[54] PHASE-CONTRAST X-RAY IMAGING SYSTEM

[75] Inventor: Atsushi Momose, Hatoyama-Machi, Japan

[73] Assignee: Hitachi, Ltd., Tokyo, Japan

[21] Appl. No.: 09/204,154

[22] Filed: Dec. 3, 1998

Related U.S. Application Data

[63] Continuation of application No. 08/827,535, Mar. 28, 1997.

[30] Foreign Application Priority Data

Mar. 29, 1996 [JP] Japan ................................. 8-075859

[51] Int. Cl.[6] ................................................. G03H 5/00
[52] U.S. Cl. ................................................. 378/36; 378/37
[58] Field of Search ................................. 378/36, 37, 84, 378/85, 145, 208

[56] References Cited

U.S. PATENT DOCUMENTS

| | | | |
|---|---|---|---|
| 3,393,314 | 7/1968 | Spielberg | 378/36 |
| 3,407,296 | 10/1968 | Armstrong | 378/36 |
| 3,439,164 | 4/1969 | Spielberg et al. | 378/36 |
| 3,446,961 | 5/1969 | Bonse et al. | 378/36 |
| 4,174,478 | 11/1979 | Franks | 378/36 |

FOREIGN PATENT DOCUMENTS 4-348262  12/1992  Japan .

OTHER PUBLICATIONS

"Phase–Contrast Radiographs of Nonstained Rat Cerebellar Specimen", by A. Momose, Med. Phys. 22, pp. 375–379 (1995).

"Phase–Contrast X–Ray Computed Tomography for Observing Biological Specimens and Organic Materials", by A. Momose, Rev. Sci. Instrum. 66, pp. 1434–1436.

"Digital Wavefront Measuring Interferometer for Testing Optical Surfaces and Lenses", by J. H. Bruning et al, Applied Optics, pp. 2693–2703 (1974).

"The Skew–Symmetric Two–Crystal X–Ray Interferometer", by P. Becker et al, J. Appl. Cryst. 7, 593 (1974).

*Primary Examiner*—David P. Porta
*Attorney, Agent, or Firm*—Antonelli, Terry, Stout & Kraus, LLP

[57] ABSTRACT

A phase-contrast X-ray imaging system according to the present invention comprises an X-ray interferometer, wherein X-ray interfering beams thicker than 2 cm×2 cm are formed enabling observation of comparatively large objects. The X-ray interferometer is constituted by two crystal blocks which each are monolithically cut out from ingots of crystal and have two wafers which function as X-ray half mirrors. An optical equipment, a chamber, and a feedback system are incorporated to adjust and stabilize the crystal blocks. A device is also incorporated to obtain an image showing the distribution of the X-ray phase shift with which diagnosis become easier and reliable.

24 Claims, 9 Drawing Sheets

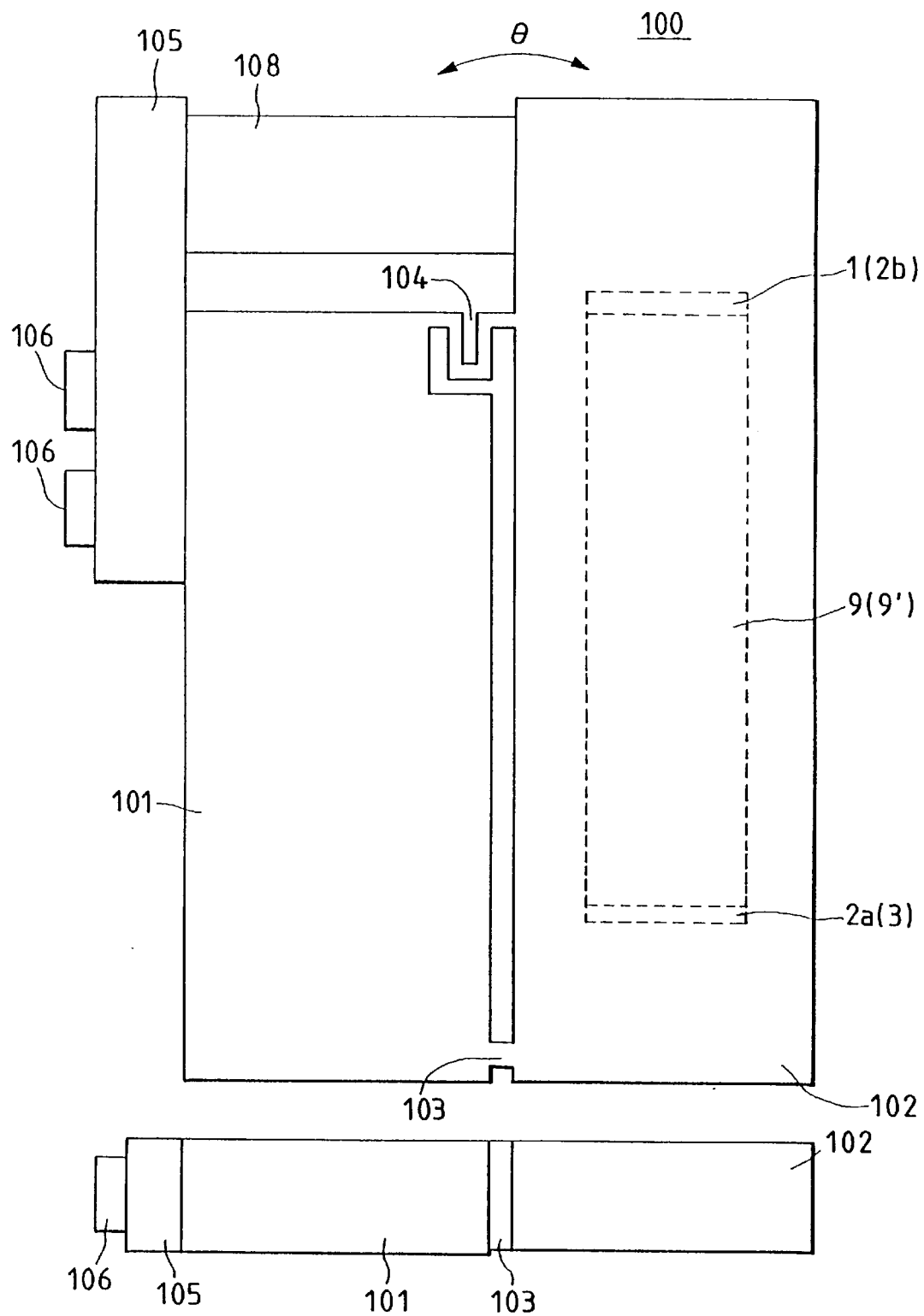

PHASE-CONTRAST X-RAY IMAGING SYSTEM

CROSS REFERENCE TO RELATED APPLICATION

This is a continuation of U.S. application Ser. No. 08/827,535, filed Mar. 28, 1997, the subject matter of which is incorporated by reference herein.

BACKGROUND OF THE INVENTION

1. Field of the Invention

The present invention relates to a phase-contrast X-ray imaging system, in detail relates to an X-ray imaging system which provides extremely high sensitivity compared with that provided by a conventional type X-ray imaging method depending upon absorption contrast. The phase-contrast X-ray imaging system according to the present invention is suitable for observing biological soft tissues and others whose X-ray absorbing power is small and provides a relatively wide view field, enabling medical diagnosis.

2. Description of the Related Art

All currently realized X-ray clinical imaging systems obtain an image contrast based upon the quantity of absorbed X-rays. Because heavier elements absorb more X-rays, an object containing more heavy elements creates clearer X-ray shadow. However, an object made of light elements (soft tissues, etc.) which does not absorb X-rays so much is too transparent for X-rays to create a sufficient contrast. When such an object is needed to be investigated with conventional clinical X-ray imaging systems, a contrast medium containing heavy elements is injected into a soft tissue although such an injection procedure is not always possible. In the case of an X-ray imaging system for diagnosing breast cancer (mammography), one compromises to use relatively low-energy X-rays to increase the sensitivity to soft tissues (in this case, breast cancer), because it is difficult to emphasize breast cancer with a contrast medium. Using low-energy X-rays bases on the fact that X-ray absorption coefficient is inversely proportional to the third power of X-ray energy and that comparatively clear contrast appears. However, as the dose of X-rays is also inversely proportional to the third power of X-ray energy, one has to compromise the increase in the dose of X-rays caused by using low-energy X-rays. Nevertheless, quality of obtained images is not always sufficient for medical diagnosis.

On the other hand, there is an imaging method for obtaining a contrast from X-ray phase shift instead of X-ray absorption. As the interaction cross section of the X-ray phase shift is approximately a thousand times as large as the interaction cross section of X-ray absorption for light elements, observation is possible with sensitivity several hundreds times higher than the absorption-contrast method. This suggests that weakly X-ray absorbing objects can be observed without using special contrast media, and the sensitivity of phase-contrast X-ray imaging was demonstrated experimentally using an X-ray interferometer. However, there is no X-ray interferometer whose size is sufficiently large for a clinical use. Several-millimeter view field has ever been realized in Phase-contrast X-ray radiography (A. Momose, et al., Med. Phys., 22, 375–380 (1995)) and Phase-contrast computed tomography (A. Momose, et al., Rev. Sci. Instrum. 66, 1434–1436 (1995), the U.S. Pat. No. 5,173,928).

Currently known typical X-ray interferometers are monolithically cut out from an ingot of single crystal of silicon or others as shown in FIG. 1. Three wafers 1 to 3 are formed in parallel each other with the same gap between them. When an incident X-ray beam 4 satisfies the Bragg diffraction condition for lattice planes 5, the incident X-ray beam 4 is separated into two beams 6a and 7a. The beam 6a is similarly separated into two beams 6b and 6c and the beam 7a into two beams 7b and 7c by the second wafer 2. The beams 6b and 7b are mixed by the third wafer 3 and interfere each other. That is, the three wafers 1 to 3 function as X-ray half mirrors, and two paths of interfering beams are formed. When an object 8 is inserted in one of the paths of the interfering beams, for example the beam 6b, the phase of the beam shifts and an interference pattern is formed in X-ray beams 6d and 7d outgoing from the third wafer 3. As the size of a view field is equivalent to the thickness of X-ray beams through the interferometer and two beam paths 6a to 6b and 7a to 7b are required to be spatially separated completely, a large interferometer is needed to provide a large view field. Estimating from the size of silicon ingots currently available, the maximum view field is approximately 2 cm×2 cm.

An X-ray interferometer comprising separated two crystal blocks which each have two X-ray half mirrors was reported by P. Becker and U. Bonse in J. Appl. Cryst. 7, 593–598 (1974). They studied a basic function of the separated X-ray interferometer and reported interference patterns with a size of 4 mm×8 mm. However, no remarkable development has not been reported to provide a large view field.

SUMMARY OF THE INVENTION

To widen a view field in a phase-contrast X-ray imaging method and utilize the widened view field for medical diagnostic imaging, an large X-ray interferometer is required to be developed. The purpose of the present invention is to enable phase-contrast X-ray imaging with a large view field suitable for a clinical use. For this purpose, a phase-contrast X-ray imaging system with a view field larger than 2 cm×2 cm is invented employing the separated-type X-ray interferometer which is corresponding to but much larger than that reported by P. Becker and U. Bonse. The present imaging system contains devices for aligning separated crystal blocks, stabilizing them, and image processing on the assumption that a part of a live body is placed on a beam path.

To align separated crystal blocks properly, stages driven by piezoelectric elements are used with a help of optical equipment. Vibration and temperature drift are crucial because such perturbations detune the X-ray interferometer and as a result an interference pattern varies. To stabilize the interferometer, therefore, a generated interference pattern is used to make a feedback signal sent to the stages driven by piezoelectric elements so that changes in an interference pattern is compensated. Some mechanical devices are also incorporated into the imaging system to reduce vibration and temperature drift. As to image processing, an image conversion procedure is incorporated. One can obtain an interference pattern using an X-ray interferometer. However, it should be noted that such an interference pattern is sometimes too complicated to provide information required for diagnosis. Therefore, a technique is incorporated into a phase-contrast X-ray imaging system to obtain diagnostic information from interference patterns.

With the phase-contrast X-ray imaging system according to the present invention, phase-contrast mammography, phase-contrast angiography and phase-contrast X-ray computed tomography are enabled.

BRIEF DESCRIPTION OF THE DRAWINGS

FIG. 6 is a top and side views showing an example of the structure of a stage driven by a piezoelectric element for θ-rotation in the embodiment according to the present invention;

DESCRIPTION OF THE PREFERRED EMBODIMENTS

Figure 1:
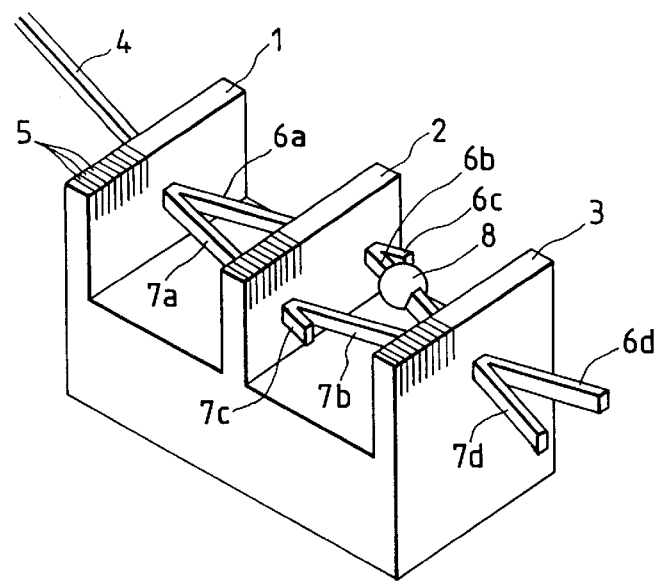
FIG. 1 shows a well-known monolithic X-ray interferometer.
Figures 2A, 2B, 2C, 2D:
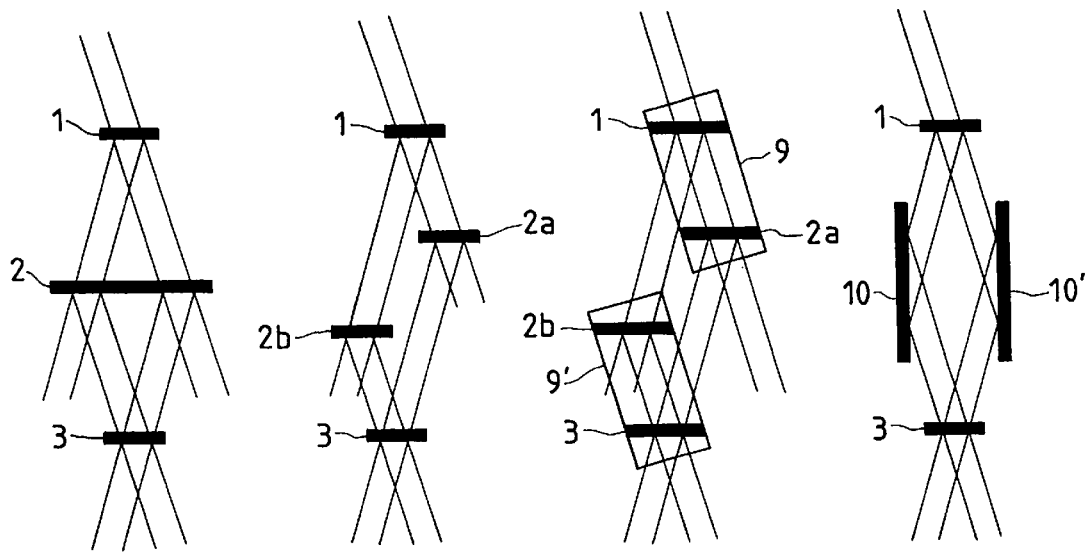
FIGS. 2(a) to (d) show beam paths created in an X-ray interferometer constituted by separated X-ray half mirrors or X-ray mirrors.

FIG. 2 shows some examples of X-ray interferometers constituted by separated X-ray half mirrors or X-ray mirrors. FIG. 2(a) shows an example in which the half mirrors 1 to 3 shown in FIG. 1 are simply separated. FIG. 2(b) shows an example in which the central half mirror is further separated into two independent half mirrors 2a and 2b and space for inserting an object (the spacing between the half mirror 2a and the half mirror 3) is expanded by shifting them in the reverse direction each other. FIG. 2(c) shows an example in which the two half mirrors 1 and 2a and the two half mirrors 2b and 3 in the example shown in FIG. 2(b) are fabricated monolithically as units 9 and 9'. FIG. 2(d) shows an example in which X-ray mirrors 10 and 10' are used in place of the central half mirror 2 in FIG. 2(a). As the central half mirrors 2, 2a and 2b shown in FIGS. 2(a) to (c) are used as mirrors to change the propagation direction of X-rays, the X-ray mirrors are used instead of half mirrors as shown in FIG. 2(d) to prevent the intensity of X-rays from being lost.

Figure 3A:
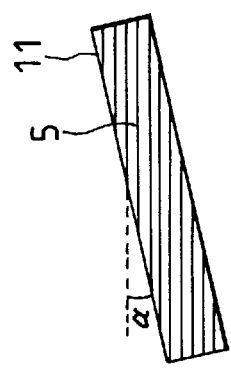
FIGS. 3(a) to (c) show the difference in the type of diffraction caused by the difference in the angle α between the crystal surface and the lattice plane related to the diffraction.
Figure 3B:
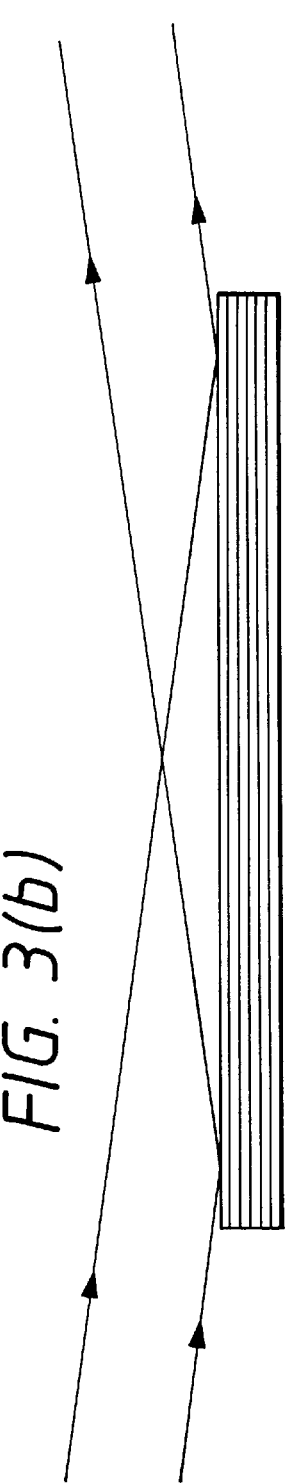
Figure 3C:
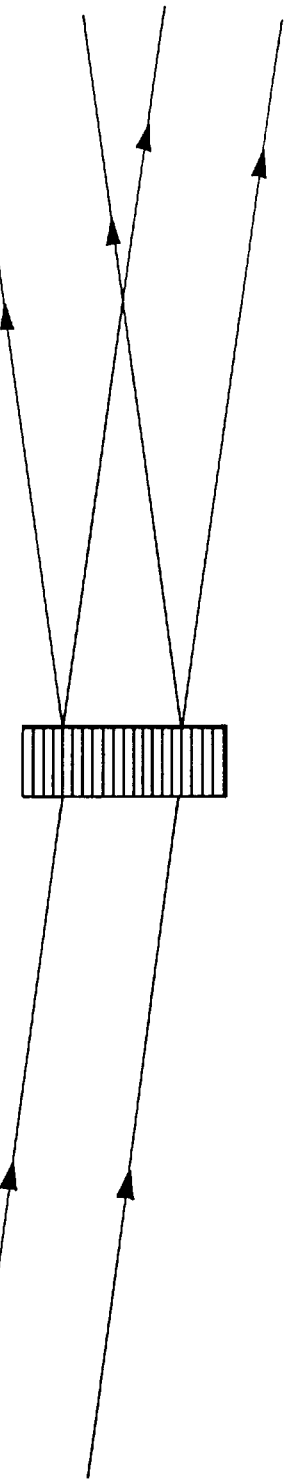

FIGS. 3(a) to (c) are schematic drawings showing the difference in the type of diffraction depending upon the difference in the angle a between the crystal surface and the lattice plane and show the difference between the X-ray mirror and the X-ray half mirror made of crystal. Lattice planes 5 of crystal related to diffraction is shown by lines with a constant spacing. Letting the angle between the crystal surface 11 and the lattice plane 5 to be 'α' as shown in FIG. 3(a), the crystal functions as an X-ray mirror as shown in FIG. 3(b) when Bragg diffraction angle θB satisfies α<θB (α=0° in this case). When α>θB, the crystal functions as an X-ray half mirror as shown in FIG. 3(c) (α=90° in this case). Full lines including an arrow indicate an incident or outgoing X-ray beam path in these drawings. In the case of FIG. 3(b), X-rays satisfying the Bragg diffraction condition is reflected with reflectivity of 80% to 90% and efficiency as an X-ray mirror is excellent, compared with that in the case of FIG. 3(c). However, there is inconvenience that a long surface is required to reflect a thick beam as in the present invention.

Other constitutions for separated-type interferometers may exist. In any case, it should be considered that the lengths of the paths of two interfering beams are substantially equal each other. This is because the coherence of an X-ray beam is generally not complete; the larger the difference in the length of X-ray beam paths is, the more coherence is deteriorated and the more the visibility of interference fringes is decreased.

In the case of any constitution shown in FIG. 2, the relative position between each X-ray half mirror or between each X-ray mirror is required to be adjusted with precision smaller than the wavelength of X-rays. A mechanism for satisfying the Bragg diffraction condition is also required.

Embodiment

Figure 4:
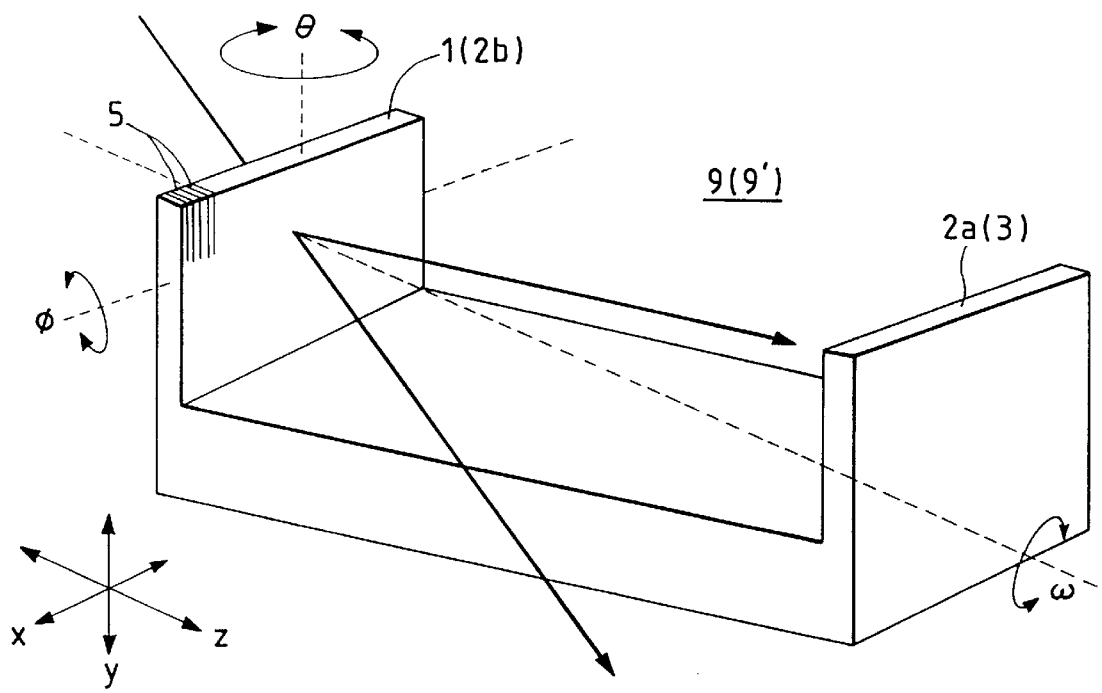
FIG. 4 shows the shape of an X-ray half mirror unit used in the embodiment according to the present invention and X-ray beam paths.

FIG. 4 shows the shape of an X-ray half mirror unit used in this embodiment of a phase-contrast mammographic system according to the present invention. X-ray half mirror units 9 and 9' are placed as shown in FIG. 2(c). Thick full lines with arrows in FIG. 4 show X-ray beam paths incident on the center of the half mirror and outgoing from the center. The direction normal to the lattice plane 5 is defined as x-axis, the direction normal to the scattering plane (a plane including the arrows showing the propagation directions of X-ray beams in the drawing) as y-axis, and the direction perpendicular to the x-axis and y-axis as z-axis. Rotation axes around x-, y- and z-axes are φ-axis, θ-axis and ω-axis, respectively. If an X-ray interferometer is constituted by the two X-ray half mirror units, there is an advantage that linear displacements in the x-, y- and z-directions do not influence interference and that adjustment is not required for linear displacement. This is because the two X-ray half mirrors on the units 9 and 9' shift in the same direction with the same distance due to the linear displacement; an effect upon the phase of an X-ray beam is canceled out.

In the meantime, when units with 80-cm gap between X-ray half mirrors are used with (440) reflection, precision smaller than $1\times10^{-10}$ radian is required for θ-rotation. For ω-rotation, precision smaller than $1\times10^{-7}$ radian is required with conditions that the gap between X-ray half mirrors on the units is 80 cm, (440) reflection is used, X-ray wavelength is 0.2 Å, and the distance between an X-ray source and an X-ray image sensor is 10 m. For φ-axis, particularly severe fine adjustment is not required. Only ω- and θ-rotations are required to be adjusted.

Figure 5:
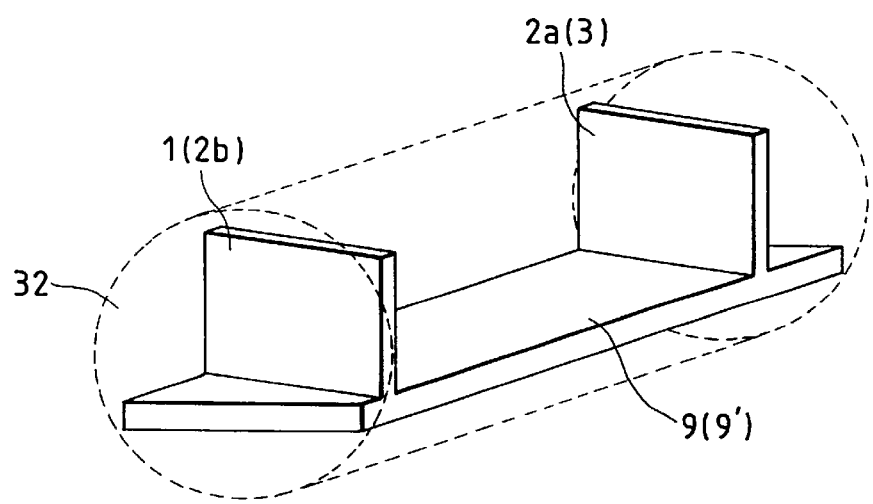
FIG. 5 shows a geometrical relation between the X-ray half mirror unit shown in FIG. 4 and a cylindrical silicon ingot from which the unit is monolithically cut out.

As shown in FIG. 5, the units 9 and 9' are carved from an ingot 32 of single crystal. If a FZ silicon with the diameter of six inches is used, an X-ray half mirror unit with a 80-cm gap between wafers can be carved providing a view field of 10 cm×10 cm. As a beam is required to be propagated substantially along the longitudinal directions of the units 9 and 9' as shown in FIG. 2(c), some limitations are imposed in choosing the growth axis of the ingot and the lattice plane related to diffraction. For example, an ingot grown in the direction tilted by six degrees from <111> axis to <110> axis is required to create a large view field efficiently when 60-keV X-rays are used with (440) reflection.

FIG. 6 is a top and side views showing an example of the structure of a stage 100 for θ-rotation in the embodiment. The stage 100 has a weak link 103 connecting a fixed part 101 and a movable part 102. A part 104 connects the parts 101 and 102 as well and functions as a spring. This structure is fabricated for example by wire-cutting a thick plate. A holding piece 105 is fixed on the side of the fixed part 101 by supporting bolts 106. A piezoelectric element 108 is put between the side of the movable part 102 and the holding piece 105. The unit 9 or 9' is put on the movable part 102 as shown by broken lines in FIG. 6. By applying voltage to the piezoelectric element 108, the piezoelectric element 108 stretches and pushes the movable part 102. Consequently, the movable part 102 rotates with a lever motion around the weak link 103 against the fixed part 101.

The stage 100 is constituted so that the bottom of the movable part 102 is a little lifted from the bottom of the fixed part 101 as the side view shows. Hereby, the movable part 102 can be smoothly rotated without friction. The fixed part 101 and movable part 102 may be formed separately. In this case, the parts are connected with pieces instead of the weak link 103 and the spring part 104.

Figure 7A:
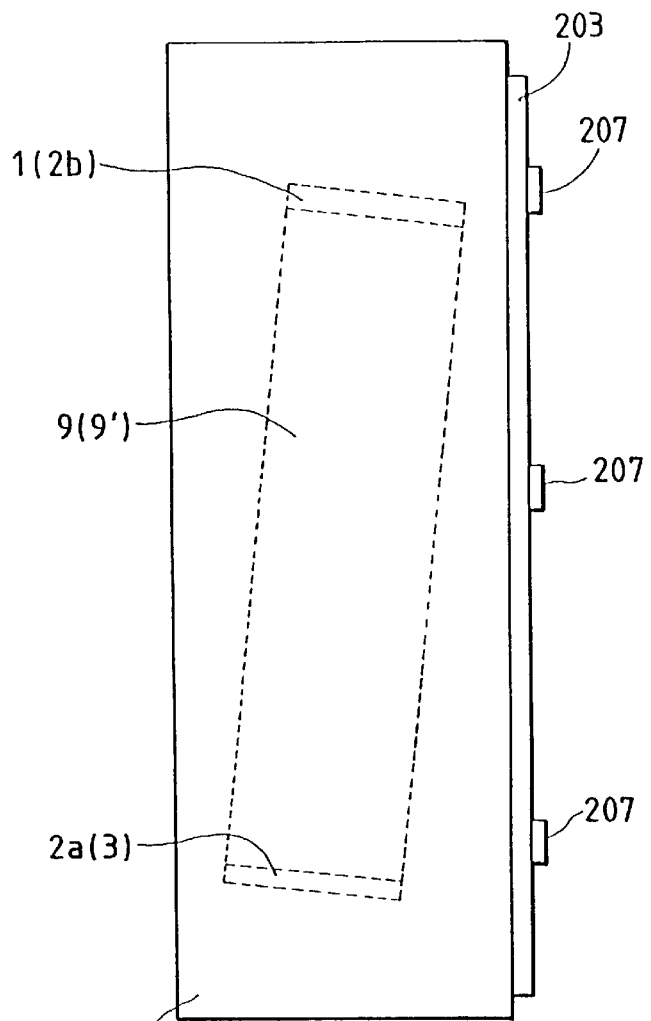
FIG. 7 is a top and side views showing an example of the structure of a stage driven by a piezoelectric element for ω rotation in the embodiment according to the present invention.
Figure 7B:
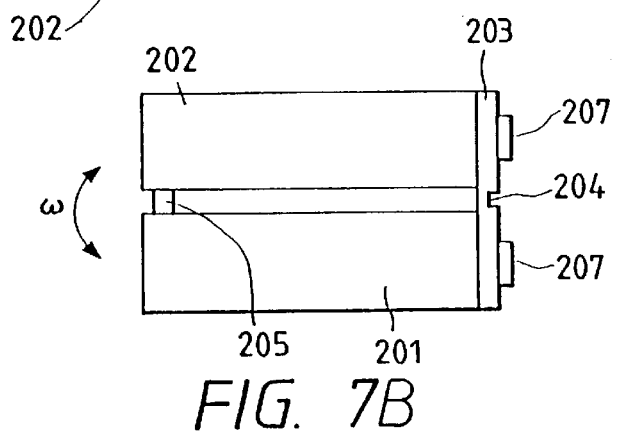

FIG. 7 is a top and side views showing an example of the structure of a stage 200 for ω-rotation in the embodiment. The side of each thick plate is connected by a connecting piece 203 so that one of two thick plates functions as a fixed part 201 and the other thick plate functions as a movable part 202. The connecting piece 203 links both parts with bolts 207 and a narrowed part 204 is formed to make the connecting piece 203 flexible. A piezoelectric element 205 is put between the fixed part 201 and movable part 202. The unit 9 or 9' is put on the surface of the movable part 202 as shown by broken lines in FIG. 7. By applying voltage to the piezoelectric element 205, the piezoelectric element 205 stretches and pushes up the movable part 202. Consequently, the movable part 202 rotates with a lever motion around the narrowed part 204.

As described above, in this embodiment, adjustment of θ-axis and ω-axis is important. By heaping the stage for ω-rotation shown in FIG. 7 on the movable part 102 of the stage for θ-rotation, a stage for tuning the units 9 and 9' is constructed.

Next, a method for obtaining diagnostic information from interference patterns will be described.

An interference pattern shows contours of constant X-ray phase shifts caused by an object. The magnitude of the X-ray phase shift greatly depends upon the shape of the object in addition to inside structures and is also influenced by the phase difference between two beams formed in an interferometer, which is zero if an interferometer is ideally constituted but normally non-zero because of adjusting error. Therefore, for example, a cancerous tissue does not always appear with a specific contrast. The contrast varies easily depending upon the size of a tumor and upon errors in alignment of an X-ray interferometer. As a contrast of a normal tissue also similarly varies, it is difficult to detect a specific focus such as cancer only based upon an interference pattern.

In the case of a conventional method depending on absorption contrast, image contrast do not basically vary due to the change in the condition of X-ray optics. The image contrast is never inverted as in interference patterns. This is because the projection of an X-ray absorption coefficient which is characteristic of a substance determines image contrast. In the case of the phase contrast method according to the present invention, X-ray interference patterns should be converted to an image which maps the distribution of a value related to the X-ray phase shift process. Here, it should be remarked that the X-ray phase shift is the projection of the refractive index and independent of the condition of the X-ray interferometer. This means that if one can obtain the distribution of the phase shift from X-ray interference patterns, diagnostic information can be extracted comparatively easily. Therefore, a method of obtaining an image showing the distribution of the X-ray phase shift from X-ray interference patterns is incorporated in the present invention.

Some methods for determining the phase shift from interference patterns are established in the field of research on visible-light interferometry. One of them, which is called the fringe-scanning method (J. H. Bruning, et al., Appl. Opt., 33, 2693–2673 (1974)), can be expanded for the X-ray interferometer used in the present invention. The distribution of the X-ray phase shift is calculated from plural interference patterns obtained with the procedure of the fringe scanning method. To adopt the fringe scanning method, a tunable X-ray phase shifter is necessary to change the phase difference between two interfering X-ray beams. When M interference patterns are obtained by changing the phase difference in 2π/M steps, the distribution of the phase shift is obtained by calculating the argument of Expression $$\sum_{k=1}^{M} I_k \exp\left(-2\pi i \frac{k}{M}\right), \quad (1)$$

where $I_k$ denotes the interference pattern obtained when the phase difference is set to $2\pi_M$ and i denotes the imaginary unit.

FIG. 8 shows examples of tunable phase shifters arranged in the beam paths of an X-ray interferometer for executing the fringe-scanning method. FIG. 8(a) shows a wedge phase shifter 25 movable in the direction of the wedge slope. By moving the wedge 25 as shown by an arrow in FIG. 8, the phase difference proportional to the distance of the wedge displacement is generated, because the X-ray phase shift is proportional to the thickness of the phase shifter. However, this phase shifter generates phase gradient in an X-ray beam, and as a result, generates interference fringes with a constant spacing. There is no problem in principle because a desired image (an image showing the distribution of the X-ray phase shift caused by an object) is obtained if the phase gradient is measured in advance without the object and subtracted from the image showing the distribution of the X-ray phase shift obtained with the object in the view. However, if the precision of fringe scanning is bad, the interference fringes caused by the wedge 25 produce a striped artifact in the image showing the distribution of the X-ray phase shift. FIG. 8(b) shows a plate phase shifter 26. By rotating the plate phase shifter 26, the phase difference is varied. As the plate phase shifter 26 itself generates no interference pattern, there is no anxiety that an artifact is formed as in FIG. 8(a). However, the rotation angle of the plate phase shifter 26 is not in proportion to the generated phase difference, and therefore, the relation between the rotation angle and the generated phase difference must be calibrated beforehand.

Figure 8A:
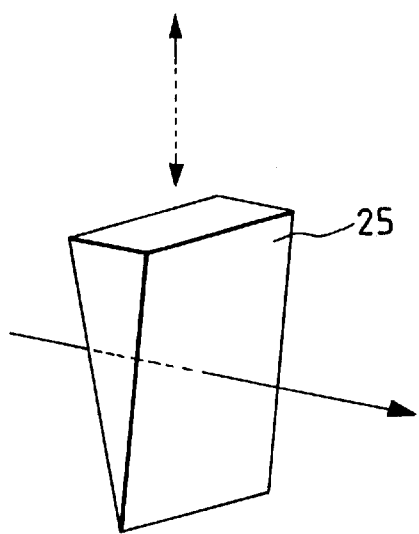
FIGS. 8(a) to (d) show constitutions of phase shifters used for the fringe scanning method.
Figure 8B:
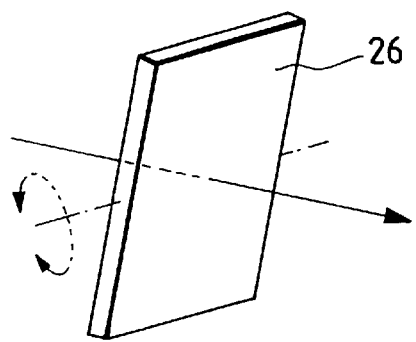
Figure 8C:
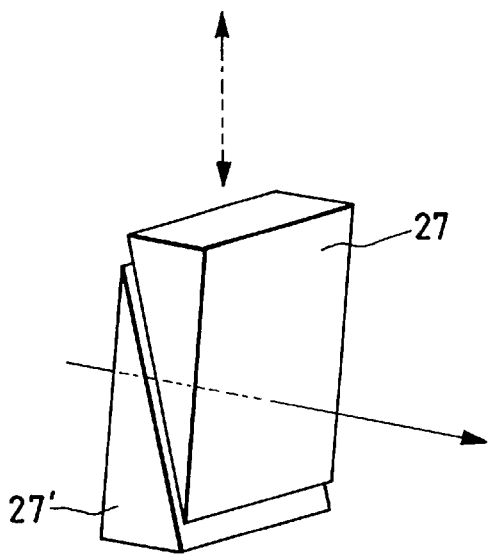
Figure 8D:
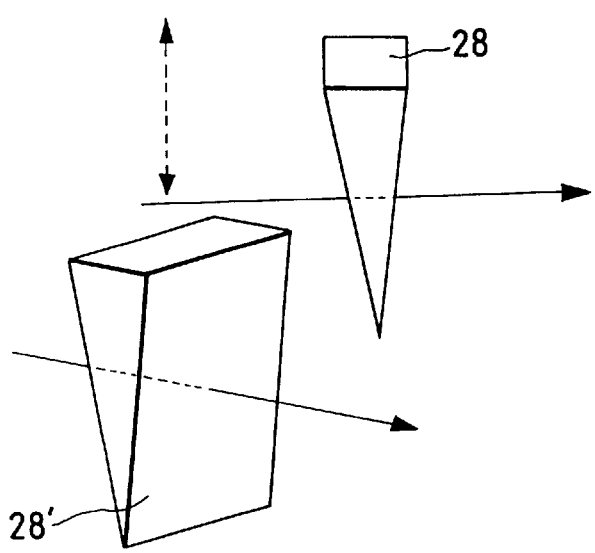

FIG. 8(c) shows a phase shifter consisting of two wedges 27 and 27' of the same shape which are piled with anti-parallel arrangement. The phase difference is adjusted by moving at least one wedge in the direction of wedge slope. This constitution has an advantage over FIG. 8(b) that the quantity of the displacement of the wedge is in proportion to the generated phase difference and an advantage over FIG. 8(a) that there is no anxiety that the striped artifact is formed. In any of the above (a), (b) and (c), the described phase shifters are inserted in one of beam paths of interfering X-rays. A set of wedges 28 and 28' shown in FIG. 8(d) is also used for the same purpose as that in FIG. 8(c). In the case of FIG. 8(d), wedges 28 and 28' of the same shape are inserted in two interfering beams respectively with the same orientation. To adjust phase difference, at least one wedge has to be moved in the direction of wedge slope.

The purpose of the present invention is to embody a phase-contrast X-ray imaging system employing an X-ray interferometer where interfering X-ray beams are thick and the beam paths are long enough for observing a part of a living body. As mentioned, in some cases, an X-ray interference pattern is not useful for diagnosis as it is. Therefore, a measure for using the fringe scanning method is incorporated to obtain an image showing the distribution of the X-ray phase shift from X-ray interference patterns, enabling the extraction of information needed for diagnoses. New diagnostic methods such as phase-contrast mammography and phase-contrast angiography can be realized using the system according to the present invention. Furthermore, phase-contrast X-ray computed tomography can be realized by obtaining and processing images showing the distribution of the X-ray phase shift measured from plural directions of projection by rotating the object. A soft tissue such as a cancer in a living body which is difficult to diagnose using the conventional absorption-contrast method can be investigated with sensitivity approximately a thousand times as high as that of the conventional method. X-ray dose on a body can be reduced greatly as well compared with that needed with the conventional method. Furthermore, as an X-ray beam through the X-ray interferometer is substantially a plane wave, an image is hardly dimmed and spatial resolution smaller than 50 $\mu$m is achieved.

Figure 9:
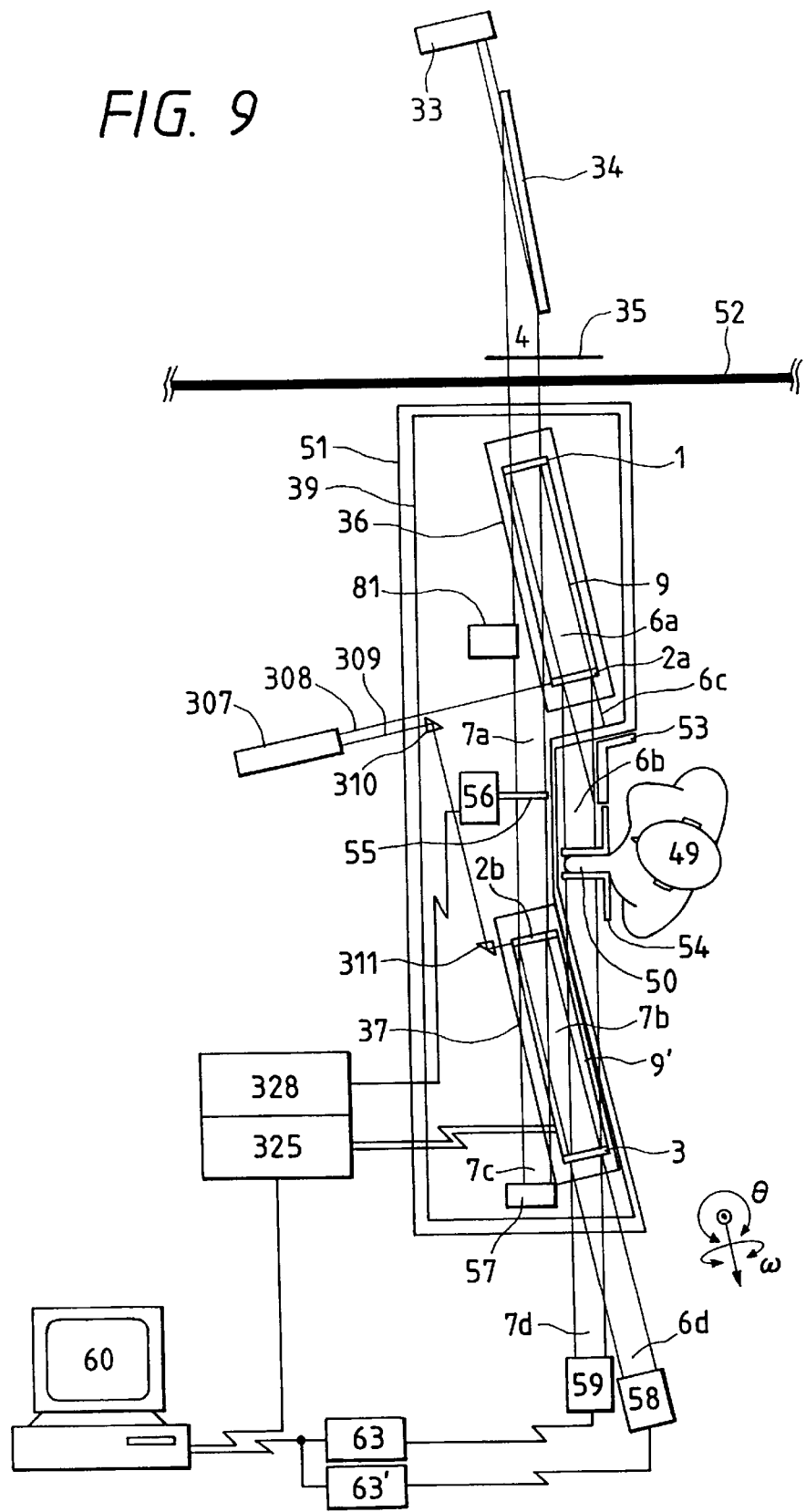
FIG. 9 is a top view showing the whole constitution of a phase-contrast mammographic system equivalent to the embodiment according to the present invention.

FIG. 9 shows a mammographic system constituted using the units comprising the X-ray half mirrors described in FIG. 4. Each unit is put on stages 36 and 37. In this embodiment, the stage 36 has a mechanism of $\theta$-rotation shown in FIG. 6, and the stage 37 has mechanisms both of $\theta$-rotation and $\omega$-rotation constituted by heaping stages described in FIGS. 6 and 7. As the relative angular position between the units 9 and 9' is needed to be tuned around $\theta$- and $\omega$-axes, replacing the stage mechanism each other between the stages 36 and 37 is also possible. The stages 36 and 37 are arranged on a table 39, and the whole system is housed in a chamber 51 to isolate the interferometer from outside air and a subject 49. In FIG. 9, only the outside line of the chamber is shown. The side facets of the units 9 and 9' are polished to be used for rough adjustment of the unit 9' (the X-ray half mirrors 2b and 3) and the unit 9 (the X-ray half mirror 1 and 2a). By seeing the polished side facets with an autocollimator 307, the units 9 and 9' are adjusted to be almost parallel each other. Light 308 emitted from the autocollimator 307 is reflected on the side facet of the unit 9 and returned to the autocollimator 307. Light 309 is reflected on the side facet of the unit 9' via prisms 310 and 311 and returned to the autocollimator 307. Angular displacements around $\theta$- and $\omega$-axes are measured by examining positions of the lights 308 and 309 returned to the autocollimator 307. The polished facets of the units 9 and 9' should be crystallographically the same to make the procedure of the rough adjustment meaningful. Of course, the units 9 and 9' must be fabricated carefully to have the same shape. In addition, inevitable fabrication errors must be calibrated in advance using X-ray diffraction. To see the side facets of the units 9 and 9' simultaneously with the autocollimator 307, the light 309 is shifted using a set of the prisms 310 and 311. In this case, the influence due to fabrication errors of the prisms 310 and 311 must be calibrated beforehand as well. The detailed procedure of the rough adjustment will be described later.

An X-ray beam incident on the X-ray half mirror 1 of the unit 9 is separated into beams 6a and 7a by the X-ray half mirror 1 and the beam 6a is separated into beams 6b and 6c by the X-ray half mirror 2a. The beam 7a is separated into beams 7b and 7c by the X-ray half mirror 2b. The beam 6b and 7b are mixed by the X-ray half mirror 3 and interference is observed in outgoing beams 6d and 7d. A mamma 50 of a subject 49 is put in the path of the beam 6b where a concave portion is made on the table 39 and the chamber 51. A shield plate 53 is installed at a part of the chamber 51 to prevent the beam 6c from reaching to the subject 49. If a concave is made on the side of the beam 7a, the same diagnosis is possible by placing a mamma 50 on the path of the beam 7a. The mamma 50 is pressed to a constant thickness by a holder 54 which is for example fixed to the floor. However, it is desirable that the holder can be moved and rotated to some extent, because flexibility for imaging increases. Reference numbers 55 and 56 respectively denote a phase shifter and its driver. The phase shifter 55 is installed in the path of the beam 7a to obtain an image showing the distribution of the X-ray phase shift with the fringe-scanning method. The driver 56 is fixed on the ceiling of the chamber 51 to prevent vibration caused by the driver 56 from being transmitted to the table 39. The phase shifter 55 is driven by a signal from a controller 328 connected to a computer 60. Reference numbers 57 and 58 denote X-ray intensity monitors for measuring the intensities of the beam 7c and 7d. A reference number 81 denotes an X-ray intensity monitor arranged in the edge of a predetermined position of the beam 7a to receive a part of X-rays of the beam 7a. For example, PIN diode detectors are used for the X-ray intensity monitors 57, 58 and 81 which output current signals proportional to the X-ray intensity incident to the monitors. The X-ray intensity monitors 57, 58 and 81 are used to align the units 9 and 9' properly. The interference pattern in the beam 7d is detected with a two-dimensional X-ray sensor 59 in this embodiment. In addition, because one can observe the same X-ray interference pattern in the beam 6d as that appearing in the beam 7d, the beam 6d can be used to make feedback signals for stabilizing the interferometer by employing another two-dimensional X-ray sensor instead of a simple intensity monitor on the position of the beam 6d. Considering the monitor 58 is a two-dimensional X-ray sensor in this embodiment, the sensors 58 and 59 are driven by controllers 63' and 63 connected to the computer 60. Interference patterns are acquired with the procedure defined in a control program run in the computer 60 and stored in the memory of the computer 60 via controllers 63' and 63. The interference patterns are analyzed by the computer 60 and used for diagnosis and for generating feedback signals to the controller 325 for stabilizing the interferometer. Following the feedback signal from the computer 60, the controller 325 changes the voltages applied to the piezoelectric elements used in the stage 37. Algorithm of this feedback will be described later.

It is desirable that X-rays incident to the X-ray half mirror 1 of the unit 9 are supplied through a partition 52 from an X-ray source 33 put in another room. This is because unnecessary radiation on the subject 49 can be reduced and vibration caused by the X-ray source 33 can be prevented from being transmitted to the X-ray interferometer.

An X-ray beam 4 is extracted with a specific energy from X-rays emitted from the X-ray source 33 by using a monochromator crystal 34 and introduced to the imaging system. The monochromator crystal 34 simultaneously widens the width of the beam 4 by asymmetric reflection (as in the case of $0<\alpha<\theta B$ in FIG. 3(a)). It is desirable that the diffraction index is the same as that of the X-ray half mirrors, and (220), (440), (400), (422) and others are practically useful. The shape of the X-ray source is set to be a line parallel to the paper surface of the drawing of FIG. 9, because the width of the X-ray beam is widened easily by the monochromator crystal 34. Consequently, intense X-ray beams are formed in the interferometer. A shutter 35 is installed between the monochromator crystal 34 and the partition 52 to prevent unnecessary X-ray exposure during intervals of image acquisitions. This shutter 35 can be installed between the X-ray source 33 and the monochromator crystal 34 as well.

Next, procedures for rough adjustment and feedback control for stabilizing the interferometer will be described. First of all, the X-ray half mirror 1 must satisfy the Bragg diffraction condition for the X-ray beam 4. Unless the $\theta$-axis of the stage 36 is tuned well, the beam 7a does not formed. The intensity monitor 81 is used to adjust the $\theta$-axis of the stage 36 to a proper angular position where the intensity of the beam 7a is maximum. Next, by using an autocollimator 307, the side facets of the unit 9 and the unit 9' are set to be parallel each other, adjusting $\theta$- and $\omega$-axes of the stage 37. After the above rough adjustment, the voltages applied to the two piezoelectric elements for $\theta$ and $\omega$ rotations of the stage 37 are scanned until an interference pattern is sensed by the X-ray image sensor 59. Once an interference pattern is generated, diagnosis can be started after optimizing the quality of the interference pattern.

Even if an interference pattern is generated and diagnosis is started, there is a possibility that $\theta$-axis and $\omega$-axis which require high precision adjustment drift and consequently an interference pattern varies. To avoid the problem, the X-ray interferometer can be stabilized by controlling with feedback signals obtained by analyzing an interference pattern detected with the X-ray image sensor 58. The change in an interference pattern is characteristic of the drifts of $\theta$ and $\omega$ axes. In the case of $\theta$-drift, the nominal phase difference between the two beams 6b and 7b varies and interference fringes move in the direction of phase gradient. In the case of $\omega$-drift, fringes like rotation moire fringes are generated and expand or contract depending upon the quantity of the drift of $\omega$-axis. Therefore, stable diagnosis is enabled by feedback-controlling so that the change in an interference pattern detected by the X-ray image sensor 58 is compensated by changing the voltages applied to the stage 37.

When the fringe-scanning method is carried out, the control program run in the computer 60 instructs the driver 56 of the phase shifter 55 to change the phase difference step by step and instructs the controller 63 to acquire plural images (interference patterns). An image showing the distribution of the X-ray phase shift is calculated in the computer by extracting the argument of Expression (1) and displayed on the display of the computer 60.

Figure 10:
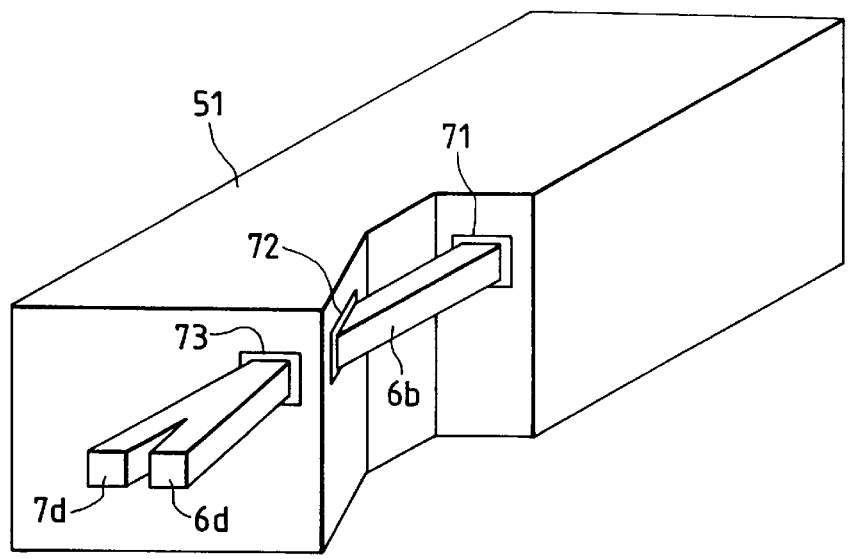
FIG. 10 is a perspective drawing showing a chamber used for the phase-contrast mammographic system equivalent to the embodiment according to the present invention.

FIG. 10 is a perspective drawing showing the chamber 51 and X-ray beams of the embodiment. The beam 6b is once led outside the chamber 51 through windows 71 and 72. A mamma 50 (not shown) is placed between the windows 71 and 72. The beams 6d and 7d are led outside the chamber 51 through a window 73 and detected. The windows 71 to 73 are made of materials such as plastic which do not absorb X-rays so much. The inside of the chamber 51 is isolated from the outside by the windows 71 to 73. Therefore, heat from a subject 49, such as body temperature and breath, does not affect the optical system inside the chamber 51. Air inside the chamber 51 can be pumped out to isolate the interferometer from outside perturbation. In FIG. 10, the incident X-ray beam 4 is not shown.

Figure 11:
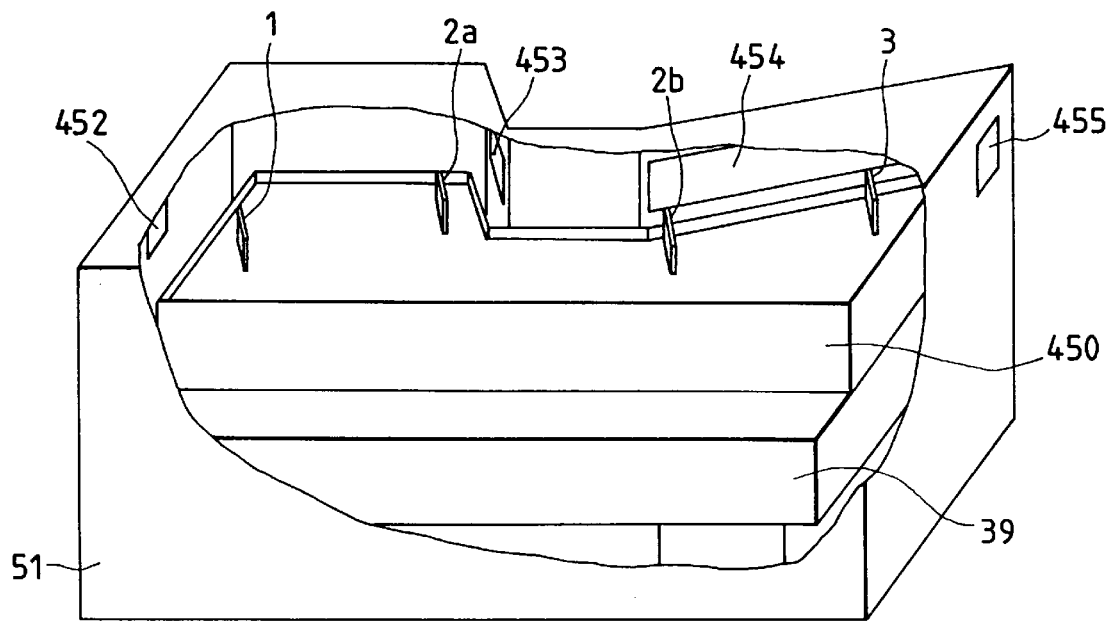
FIG. 11 is a perspective drawing showing the inside of the chamber wherein a measure for reducing vibration is added to the phase-contrast mammographic system equivalent to the embodiment according to the present invention.

FIG. 11 shows an embodiment of a phase-contrast X-ray imaging system whose constitution is the same as in the above embodiment except that a device is added to reduce vibration. If the units 9 and 9' vibrate relatively, generated interference fringes also vibrate. As a result, the visibility of an interference pattern nominally decreases and occasionally the interference pattern disappears. Therefore, a device is required so that vibration is not transmitted to the units 9 and 9'. In this embodiment, as shown in FIG. 11, the units 9 and 9' are put in a pool 450 with stages 36 and 37 below the units 9 and 9'. The pool 450 is filled with liquid of high viscosity such as oil. The height of the liquid in the pool 450 is set so that only the X-ray half mirrors 1, 2a, 2b and 3 appear above the liquid level. The pool 450 is put on the table 39 and the whole is housed in the chamber 51. Hereby, vibration is eliminated to some extent and the visibility of an interference pattern is prevented from decreasing. X-ray windows 452, 453, 454 and 455 made of beryllium are installed on the walls of the chamber 51 to prevent outside air from flowing inside the chamber. In addition, a polymer film, a thin aluminum plate, a glass plate, and so on can be used instead of beryllium. The windows 453, 454, and 455 are equivalent to the windows 71, 72, and 73 in FIG. 10, respectively.

Figure 12:
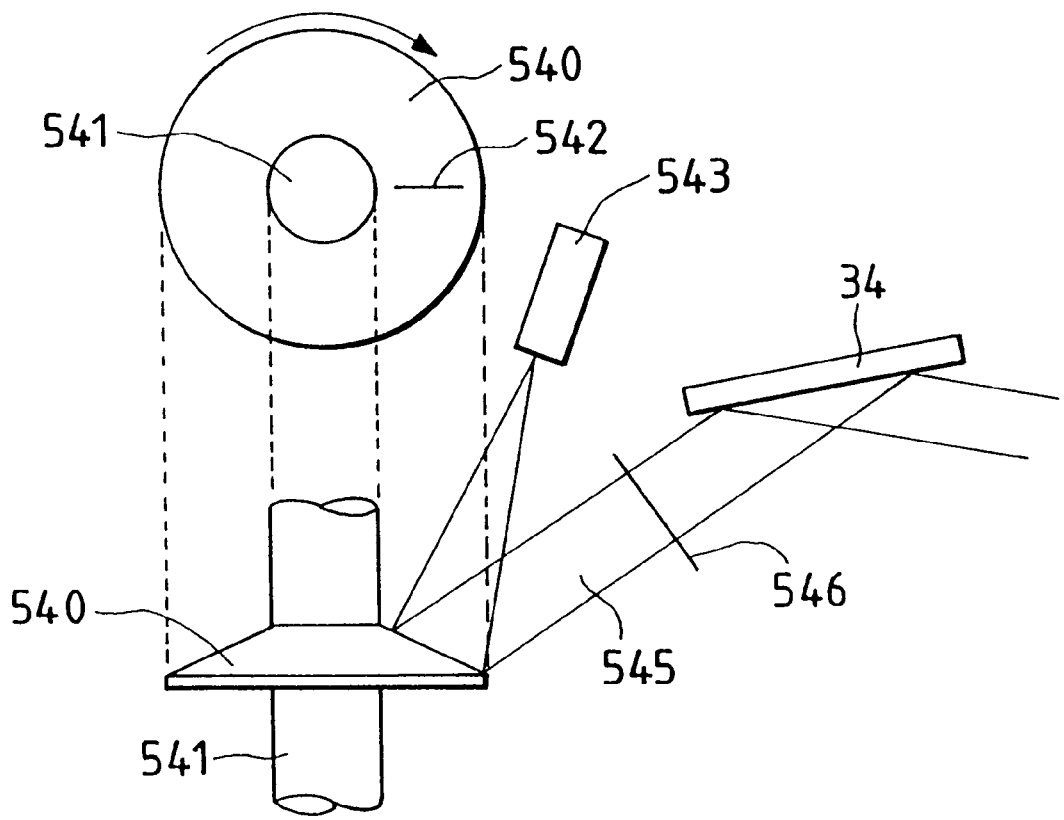
FIG. 12 shows an example of the constitution of an X-ray source with a line X-ray emitting spot and the geometrical relation between the X-rays source and a monochromator crystal used for the phase-contrast mammographic system equivalent to the embodiment according to the present invention.

FIG. 12 shows an example of an X-ray source convenient for the phase-contrast X-ray imaging system. As the X-ray interferometer functions for X-rays of a narrow energy band width, it is advantageous to use an intense X-ray source to acquire an image promptly. In the case of the X-ray optical system used in the embodiment, a line X-ray source parallel to the scattering plane of the X-ray optical system can be used. Therefore, if an X-rays source excited by an electron beam or by a laser beam is used, it is effective to constitute the X-ray source as shown in FIG. 12.

In FIG. 12, the reference number 540 denotes a target, 541 denotes a rotation axis, 542 denotes an X-ray emitting part, 543 denotes an electron beam source or a laser beam source, 544 denotes an electron beam or a laser beam, 545 denotes an X-ray beam, and 546 denotes a filter. According to this constitution, an electron beam or a laser beam 544 is linearly scanned on the target 540 and a line X-ray source can be formed. Heat load to the target 540 can be diffused by scanning the electron or laser beam, and therefore more X-rays can be let to the X-ray interferometer.

Though drawings are omitted, it is also possible to change the geometry between the monochromator crystal 34 and the X-ray interferometer so that the beam 4 is parallel to the beam 6a. Moreover, other types of monochromators comprising two or more crystals are useful instead of the monochromator crystal 34 to supply a better X-ray beam to the X-ray interferometer.

According to the present invention, as sensitivity is very high, contrast media are not required to be injected. However, to emphasize a specific interested part, contrast media are still useful. In this case, contrast media containing of heavy elements are not required to be used as in the conventional method. One can select contrast media from variety of materials.

I claim:

1. A phase-contrast X-ray imaging system, comprising:
an X-ray interferometer wherein interfering X-ray beams traveling along different paths are formed, and
a chamber in which said X-ray interferometer is installed, said chamber having a concave section for enabling one of the paths of the interfering X-ray beams to travel outside the chamber and pass through a portion of a subject provided outside of said chamber at the concave section.

2. A phase-contrast X-ray imaging system according to claim 1, wherein the one of the paths of the interfering X-ray beams after traveling outside the chamber at one part of the concave section of said chamber enters said chamber at another part of the concave section and interferes with another path of the interfering X-ray beam.

3. A phase-contrast X-ray imaging system according to claim 1, wherein said X-ray interferometer is constituted by two crystal blocks which each are monolithically cut out from ingots of crystal and have two wafers which function as X-ray half mirrors, and said crystal blocks are placed on stages which are provided on a common table in said chamber and have mechanisms for adjusting the relative position between said two crystal blocks to generate interference.

4. A phase-contrast X-ray imaging system according to claim 1, wherein a tunable phase shifter is placed at least on one of the paths of the interfering X-ray beams, and an image showing the distribution of an X-ray phase shift caused by the subject is generated from X-ray interference patterns of the interfering X-ray beams.

5. A phase-contrast X-ray imaging system according to claim 3, wherein a tunable phase shifter is placed at least on one of the paths of the interfering X-ray beams, and an image showing the distribution of X-ray phase shift caused by the subject is generated from X-ray interference patterns of the interfering X-ray beams.

6. A phase-contrast X-ray imaging system according to claim 2, further comprising a pool in which said X-ray interferometer is provided, said pool being filled with liquid of high viscosity so that said wafers of said crystal blocks are above the liquid surface of said pool.

7. A phase-contrast X-ray imaging system according to claim 3, further comprising a pool in which said X-ray interferometer and said stages for adjustment are provided, said pool being filled with liquid of high viscosity so that said wafers of said crystal blocks are above the liquid surface of said pool.

8. A phase-contrast X-ray imaging system according to claim 1, further comprising equipment for pumping air from the inside of said chamber.

9. A phase-contrast X-ray imaging system according to claim 3, further comprising equipment for pumping air from the inside of said chamber.

10. A phase-contrast X-ray imaging system according to claim 3, further comprising optical equipment used for preliminary alignment of the X-ray interferometer constituted by said crystal blocks so that said two crystal blocks are placed to a proper position to generate interference by viewing polished facets of said two crystal blocks with the optical equipment.

11. A phase-contrast X-ray imaging system according to claim 3, wherein beam intensity monitors are provided to adjust said crystal blocks, and image sensors are provided to observe interference patterns which enable both diagnosing of the subject and providing feedback signals which are sent to said stages for adjustment so that drifts in interference fringes are compensated.

12. A phase-contrast X-ray imaging system, comprising:
an X-ray interferometer wherein interfering X-ray beams thicker than 2 cm×2 cm are formed, the interfering X-ray beam traveling along different paths and
a chamber in which said X-ray interferometer is installed, said chamber having a concave section for enabling one of the paths of the interfering X-ray beams to travel outside the chamber and pass through a portion of a subject provided outside of said chamber at the concave section.

13. A phase-contrast X-ray imaging system according to claim 12, wherein the one of the paths of the interfering X-ray beams after traveling outside the chamber at one part of the concave section of said chamber enters said chamber at another part of the concave section and interferes with another path of the interfering X-ray beam.

14. A phase-contrast X-ray imaging system according to claim 12, wherein said X-ray interferometer is constituted by two crystal blocks which each are monolithically cut out from ingots of crystal and have two wafers which function as X-ray half mirrors, and said crystal blocks are placed on stages which are provided on a common table in said chamber and have mechanisms for adjusting the relative position between said two crystal blocks to generate interference.

15. A phase-contrast X-ray imaging system according to claim 12, wherein a tunable phase shifter is placed at least on one of the paths of the interfering X-ray beams, and an image showing the distribution of an X-ray phase shift caused by the subject is generated from X-ray interference patterns of the interfering X-ray beams.

16. A phase-contrast X-ray imaging system according to claim 14, wherein a tunable phase shifter is placed at least on one of the paths of the interfering X-ray beams, and an image showing the distribution of X-ray phase shift caused by the subject is generated from X-ray interference patterns of the interfering X-ray beams.

17. A phase-contrast X-ray imaging system according to claim 14, further comprising a pool in which said X-ray interferometer is provided, said pool being filled with liquid of high viscosity so that said wafers of said crystal blocks are above the liquid surface of said pool.

18. A phase-contrast X-ray imaging system according to claim 14, further comprising a pool in which said X-ray interferometer and said stages for adjustment are provided, said pool being filled with liquid of high viscosity so that said wafers of said crystal blocks are above the liquid surface of said pool.

19. A phase-contrast X-ray imaging system according to claim 12, further comprising equipment for pumping air from the inside of said chamber.

20. A phase-contrast X-ray imaging system according to claim 14, further comprising equipment for pumping air from the inside of said chamber.

21. A phase-contrast X-ray imaging system according to claim 14, further comprising optical equipment used for preliminary alignment of the X-ray interferometer constituted by said crystal blocks so that said two crystal blocks are placed to a proper position to generate interference by viewing polished facets of said two crystal blocks with the optical equipment.

22. A phase-contrast X-ray imaging system according to claim 14, wherein beam intensity monitors are provided to adjust said crystal blocks, and image sensors are provided to observe interference patterns which enable both diagnosing of the subject and providing feedback signals which are sent to said stages for adjustment so that drifts in interference fringes are compensated.

23. A phase-contrast X-ray imaging system for diagnosis of breast cancer, comprising:

an X-ray interferometer wherein interfering X-ray beams traveling along different paths are formed, said X-ray interferometer including two crystal blocks which each are monolithically cut out from ingots of crystal and have two wafers which function as X-ray half mirrors;

stages for adjusting the two crystal blocks to a proper position where interference is generated;

a table on which said stages for adjustment are provided;

optical equipment for preliminary alignment of the two crystal blocks for placing said two crystal blocks substantially to a proper position which satisfies a diffraction condition of said X-ray half mirrors by viewing polished facets of said two crystal blocks with the optical equipment;

X-ray intensity monitors for adjustment of the two crystal blocks to satisfy the diffraction condition of said X-ray half mirrors;

a tunable X-ray phase shifter placed at least on one of the paths of the interfering X-ray beams for obtaining an image showing the distribution of an X-ray phase shift caused by a subject placed on one of the paths of the interfering X-ray beams;

a chamber in which said X-ray interferometer, said stages for adjustment, said table, said X-ray intensity monitors, and said tunable X-ray phase shifter are installed, said chamber having a concave section for enabling one of the paths of the interfering X-ray beams to travel outside the chamber and pass through a portion of a subject provided outside of said chamber at the concave section;

X-ray image sensors for obtaining X-ray interference patterns of the interfering X-ray beams; and a computer for controlling said tunable X-ray phase shifter, said stages for adjustment, and said X-ray image sensors, for analyzing observed X-ray interference pasterns to provide feedback signals which are sent to the stages for adjustment so that drifts in interference fringes are compensated, and for diagnosing existence of breast cancer.

24. A phase-contrast X-ray imaging system according to claim 23, wherein the one of the paths of the interfering X-ray beams after traveling outside the chamber at one part of the concave section of said chamber enters said chamber at another part of the concave section and interferes with another path of the interfering X-ray beam.

* * * * *